United States Patent
Cohen

(10) Patent No.: US 8,273,067 B2
(45) Date of Patent: Sep. 25, 2012

(54) LEG CUT-OUT STAGES OF DEVELOPMENT

(75) Inventor: Jason C. Cohen, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1173 days.

(21) Appl. No.: 11/510,400

(22) Filed: Aug. 25, 2006

(65) Prior Publication Data

US 2008/0051747 A1   Feb. 28, 2008

(51) Int. Cl.
*A61F 13/15* (2006.01)
*A61F 13/20* (2006.01)

(52) U.S. Cl. .............. 604/385.01; 604/385.25

(58) Field of Classification Search ............ 604/385.01, 604/385.21, 385.25, 385.101, 385.16
See application file for complete search history.

(56) References Cited

U.S. PATENT DOCUMENTS

| | | | | |
|---|---|---|---|---|
| 4,536,181 | A | * | 8/1985 | Cook .................. 604/387 |
| 4,798,603 | A | | 1/1989 | Meyer et al. |
| 5,074,854 | A | * | 12/1991 | Davis ............. 604/385.11 |
| 5,704,929 | A | * | 1/1998 | Bien ............... 604/385.23 |
| 5,853,405 | A | * | 12/1998 | Suprise ............... 604/391 |
| 6,648,864 | B2 | * | 11/2003 | Ronn et al. ......... 604/385.01 |
| 2006/0069372 | A1 | * | 3/2006 | Chakravarty et al. ... 604/385.02 |

FOREIGN PATENT DOCUMENTS

EP    0 539 703 A1   5/1993

* cited by examiner

*Primary Examiner* — Michele M Kidwell
(74) *Attorney, Agent, or Firm* — David J. Arteman

(57) ABSTRACT

Manufacturers of disposable absorbent articles may produce a wide range of sizes of articles. The design of these articles has generally remained the same as the product increases in size to fit larger and larger users. Generally speaking, the proportions of the articles remain the same in smaller and larger sizes. For example, the longitudinal length of the absorbent core as a percentage of the total longitudinal length of the article may be approximately the same for small, medium, and large sizes.

21 Claims, 3 Drawing Sheets

LEG CUT-OUT STAGES OF DEVELOPMENT

BACKGROUND OF THE INVENTION

The present invention is generally related to arrays of disposable articles that are designed to be worn about the waist and legs of a user. More specifically, the present invention relates to the placement and orientation of product features to accommodate the physical development of a user, for example newborns, infants, and toddlers.

Disposable absorbent articles have long been known as personal care hygiene products. Disposable absorbent articles include infant diapers, diaper-pants, training pants, swim pants, adult incontinence pads and briefs, and women's sanitary pads. Such absorbent articles are designed and constructed to absorb and store both solid and liquid bodily excretions such as urine, feces, menstrual fluid, or blood.

Manufacturers of disposable absorbent articles may produce a wide range of sizes of these articles. The design of these articles has generally remained the same as the product increases in size to fit larger and larger users. Generally speaking, the proportions of the articles remain the same in smaller and larger sizes. For example, the longitudinal length of the absorbent core as a percentage of the total longitudinal length of the article may be approximately the same for small, medium, and large sizes. Some manufacturers have added specific features to the different sizes in order to provide for unique needs of the users. Examples include the addition of an umbilical cord feature for a newborn or a training aid for a toddler in toilet training.

An aspect that has not been addressed directly in the past by manufacturers of disposable absorbent articles is the change that takes place in the predominant position of the legs as children develop from the newborn stage through the various stages of locomotion including crawling and walking.

Accordingly, there remains a need for an array of disposable absorbent articles that accommodate the various predominant leg positions, for example the predominant leg positions of newborns, infants, and toddlers.

SUMMARY OF THE INVENTION

In general, the present disclosure is directed to an array of disposable absorbent articles and a method of providing an array of disposable absorbent articles. For example, in one embodiment, the array of disposable articles is contemporaneously manufactured by or for the same business entity. The array includes a first disposable article having a first front end edge, a first longitudinal length, and a first pair of leg openings. The first pair of leg openings has a first leg opening median located a first longitudinal distance from the first front end edge. The first pair of leg openings has a first leg opening longitudinal position ratio defined by the first longitudinal distance divided by the first longitudinal length. The array also includes a second disposable article having a second front end edge, a second longitudinal length, and a second pair of leg openings. The second pair of leg openings has a second leg opening median located a second longitudinal distance from the second front end edge. The second pair of leg opening has a second leg opening longitudinal position ratio defined by the second longitudinal distance divided by the second longitudinal length. Further, the second leg opening longitudinal position ratio divided by the first leg opening longitudinal position ratio is greater than 1.2.

Another version of the present invention includes a method of providing an array of disposable absorbent articles. The array is contemporaneously manufactured by or for the same business entity. The method includes providing an array of at least two different disposable articles. The array includes a first disposable article having a first front end edge, a first longitudinal length, and a first pair of leg openings. The first pair of leg openings has a first leg opening median located a first longitudinal distance from the first front end edge. The first pair of leg openings has a first leg opening longitudinal position ratio defined by the first longitudinal distance divided by the first longitudinal length. The array also includes a second disposable article having a second front end edge, a second longitudinal length, and a second pair of leg openings. The second pair of leg openings has a second leg opening median located a second longitudinal distance from the second front end edge. The second pair of leg openings has a second leg opening longitudinal position ratio defined by the second longitudinal distance divided by the second longitudinal length. Further, the second leg opening longitudinal position ratio divided by the first leg opening longitudinal position ratio is greater than 1.2. The method also includes conveying information to a consumer describing the predominant leg position of a user that indicates greater applicability of one of the disposable articles in the array over an other disposable article in the array.

Finally, another version of the present invention includes an array of disposable articles contemporaneously manufactured by or for the same business entity. The array includes a plurality of first disposable articles having a first similar configuration. The first disposable articles have a first front end edge, a first longitudinal length, and a first pair of leg openings. The first pair of leg openings has a first leg opening median located a first longitudinal distance from the first front end edge. The first pair of leg openings has a first leg opening longitudinal position ratio defined by the first longitudinal distance divided by the first longitudinal length. The array also includes a plurality of second disposable articles having a second similar configuration. The second disposable articles have a second front end edge, a second longitudinal length, and a second pair of leg openings. The second pair of leg opening has a second leg opening median located a second longitudinal distance from the second front end edge. The second pair of leg openings has a second leg opening longitudinal position ratio defined by the second longitudinal distance divided by the second longitudinal length. Further, the second leg opening longitudinal position ratio divided by the first leg opening longitudinal position ratio is greater than 1.2. The first pair of leg openings has portions that are arcuate. The second pair of leg openings has portions that are arcuate.

BRIEF DESCRIPTION OF THE DRAWINGS

The present invention will be more fully understood and further advantages will become apparent when reference is made to the following detailed description of the invention and the accompanying drawings wherein like numerals represent like elements. The drawings are merely representative and are not intended to limit the scope of the appended claims.

DETAILED DESCRIPTION OF THE INVENTION

Figure 1:
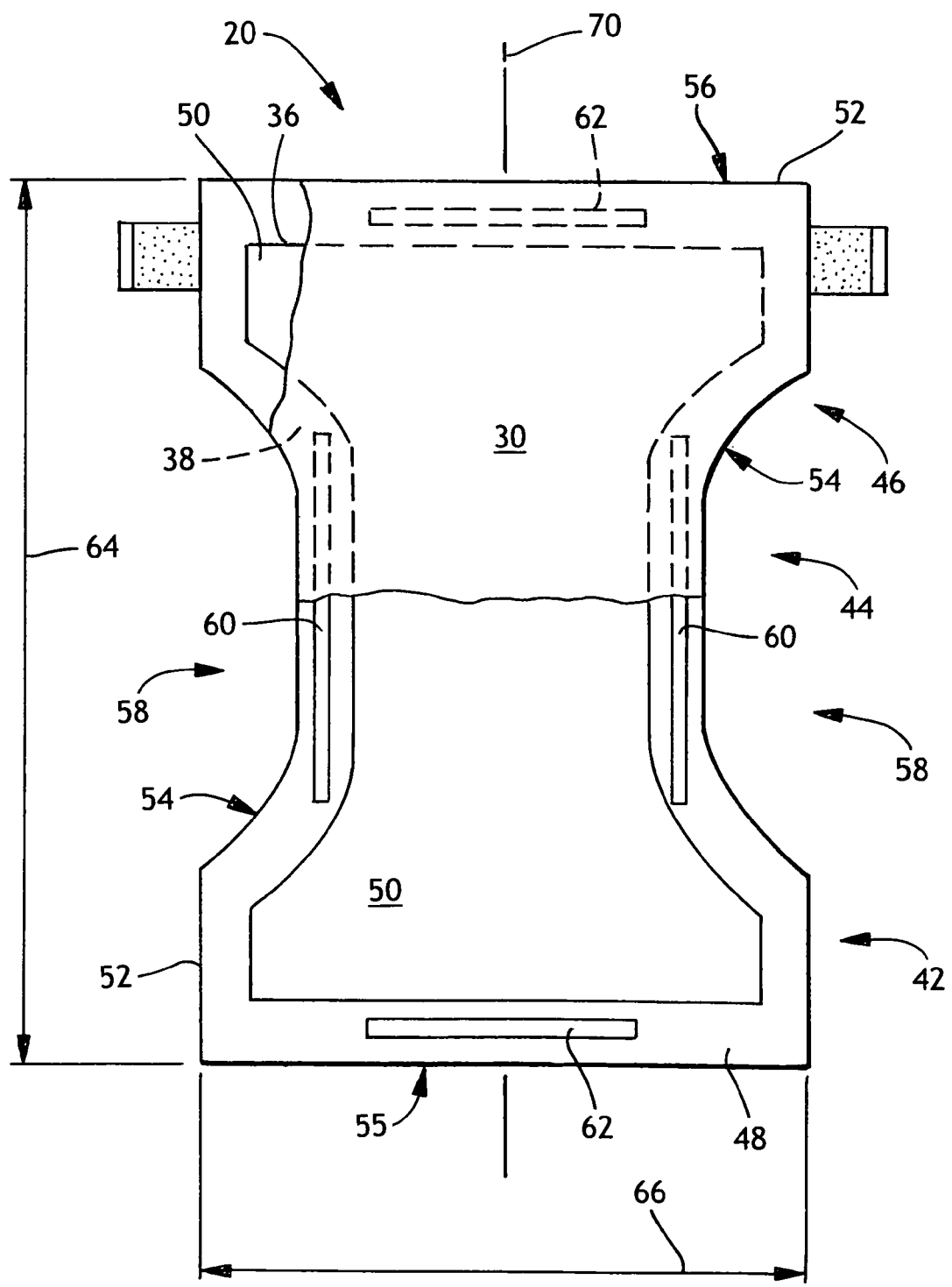
FIG. 1 illustrates a plan view of a disposable absorbent article in an unfastened, stretched, and laid flat condition with the surface of the article which contacts the wearer's skin facing the viewer and with portions of the article partially cut away to show the underlying features.

The present disclosure of the invention will be expressed in terms of its various components, elements, constructions, configurations, arrangements, and other features that may also be individually or collectively referenced by the term, "aspect(s)" of the invention, or other similar terms. It is contemplated that the various forms of the disclosed invention may incorporate one or more of its various features and aspects, and that such features and aspects may be employed in any desired operative combination thereof.

When introducing elements of the present invention or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements. "Disposed", "disposed on", "disposed with", "disposed at", "disposed near", and variations thereof are intended to mean that one element can be integral with another element, or that one element can be a separate structure bonded to or placed with or placed near another element.

The present invention is directed to an array of disposable articles and a method of providing an array of disposable articles. The array of disposable articles being contemporaneously manufactured by or for the same business entity. The method includes conveying corresponding information pertaining to the selection of the appropriate article to choose depending on the predominant leg position of a user. The information provided in this method is intended to provide a parent or caregiver, hereinafter simply referred to as a caregiver, with guidance on the selection of an appropriate absorbent article for a user based on the caregiver's knowledge of the user's developmental stage, activity level, and other personal characteristics that may have a bearing on the predominant leg position of the user.

In various aspects of the present invention, the disposable article 20', 20'', 20''' of the array may be branded with the same trademark or with different trademarks from the same trademark owner. An "owner" is defined broadly to include separate divisions or subsidiaries of a parent company or business entity. Thus, if two companies are owned by a common business entity yet own different trademarks, then the trademarks are considered to have common ownership. In one aspect of the invention, the first disposable article 20' and the second disposable article 20'' are associated with a first commonly owned trademark. One example of a trademark owned by the assignee of this invention is "HUGGIES." However, this particular mark is not critical to the present invention—any desired trademark may be used. For example, the first 20' and the second 20'' disposable article may both be marked with the HUGGIES trademark.

In various other aspects of the present invention, the first disposable article 20', the second disposable article 20'', and/or the third disposable article 20''' are marked with a commonly owned second trademark. As another non-limiting example, the first 20', second 20'' and/or third 20''' disposable article may be marked with the SUPREME trademark.

The present invention is directed to an array of disposable articles that accommodate the various predominant leg positions of users, for example, the leg positions of newborns, infants, and toddlers. This array of disposable articles is intended to provide a user with an optimum fitting disposable article regardless of the particular predominant leg position that the particular user has at a particular time of use.

The principles of the present invention can be incorporated into a series of any suitable disposable articles designed to fit around the legs and waist of a user. Examples of such suitable articles include diapers, diaper-pants, training pants, incontinence products, other personal care or health care garments including medical garments, or the like. The array may include a number of the same disposable article type, for example three diapers. Alternatively, the array may include a number of different disposable article types, for example, a diaper, a diaper-pant, and a training pant. For ease of explanation, the description hereafter will be in terms of an array of diapers.

Representative Disposable Article

The individual disposable articles that make up the array will be described in greater detail in the context of a single diaper. Typically, disposable articles are intended for limited use and are not intended to be laundered or otherwise cleaned for reuse. A disposable diaper, for example, is discarded after it has become soiled by the wearer.

FIG. 1 illustrates a disposable diaper 20 which may be incorporated into the discussed arrays. The illustrated disposable diaper 20 has a front portion 42, a rear portion 46, and a crotch portion 44 located between the front and rear portions. The disposable diaper includes an outer cover 48, a bodyside liner 30, and an absorbent structure 50 situated between the outer cover 48 and the liner 30. The outer edges of the diaper 20 define a periphery 52 with laterally opposed, longitudinally extending side edges 54; longitudinally opposed, laterally extending end edges, specifically a front end edge 55, and a rear end edge 56; and a system of elastomeric gathering members, such as a system including leg elastics 60 and waist elastics 62. The longitudinal side edges 54 define a pair of leg openings 58 for the diaper 20, and optionally, are curvilinear and contoured. The lateral end edges 55, 56 are illustrated as straight, but optionally, may be curvilinear. The diaper 20 may also include additional components to assist in the acquisition, distribution and storage of bodily exudates. For example, the diaper 20 may include a transport layer, such as described in U.S. Pat. No. 4,798,603, to Meyer et al., or a surge management layer, such as described in European Patent Office Publication No. 0539703, published May 5, 1993.

With regard to the designated surfaces of the absorbent article and its components, the various upper or bodyside surfaces are configured to face toward the body of the wearer when the absorbent article is worn by the wearer for ordinary use. The various opposing or lower surfaces are configured to face away from the wearer's body when the absorbent article is worn by the wearer.

The diaper 20 generally defines a longitudinally extending length dimension 64, and a laterally extending width dimension 66, as representatively illustrated in FIG. 1.

The outer cover 48 and the liner 30 may be generally coextensive (e.g., FIG. 1), or optionally, may be non-coextensive. Either or both of the outer cover 48 and the liner 30 may have length and width dimensions which are generally larger than those of the absorbent structure 50 and extend beyond the corresponding dimensions of the absorbent structure 50 to provide longitudinal side edges 54 and lateral end edges 55, 56 which may be connected or otherwise associated together in an operable manner. As used herein when describing the liner 30 in relation to the outer cover 48 and vice versa, the term "associated" encompasses configurations in which the liner 30 is directly joined to the outer cover 48, and configurations where the liner 30 is indirectly joined to the outer cover 48 by affixing portions of the liner 30 to intermediate members which in turn are affixed to at least portions of the outer cover 48. The liner 30 and the outer cover 48 can, for example, be joined to each other in at least a portion of the diaper periphery 52 by attachment mechanisms (not shown) such as adhesive bonds, sonic bonds, thermal bonds, pinning, stitching, or a variety of other attachment techniques known in the art, as well as combinations thereof.

Various woven and nonwoven fabrics may be used for the liner 30. For example, the liner 30 may be composed of a meltblown or spunbonded web of polyolefin fibers. The liner 30 may also be a bonded-carded web composed of natural and/or synthetic fibers. The liner 30 may be composed of a substantially hydrophobic material, and the hydrophobic material may, optionally, be treated with a surfactant, or otherwise processed, to impart a desired level of wettability and hydrophilicity. Specifically, the liner 30 may be a nonwoven, spunbond, polypropylene fabric composed of about 2.8 to about 3.2 denier fibers formed into a web having a basis weight of about 22 gsm and a density of about 0.06 g/cc.

The liner 30 may also be surface treated with about 0.3 weight percent of a surfactant mixture that contains a mixture of AHCOVEL Base N-62 surfactant and GLUCOPON 220UP surfactant in about a 3:1 ratio based on a total weight of the surfactant mixture. The AHCOVEL Base N-62 surfactant is purchased from Hodgson Textile Chemicals Inc., a business having offices in Mount Holly, N.C., and includes a blend of hydrogenated ethoxylated castor oil and sorbitan monooleate in a 55:45 weight ratio. The GLUCOPON 220UP surfactant is purchased from Henkel Corporation, Gulph Mills, Pa., and includes alkyl polyglycoside. The surfactant may also include additional ingredients such as aloe. The surfactant may be applied by any conventional means, such as spraying, printing, brush coating, foam or the like. The surfactant may be applied to the entire liner 30 or may be selectively applied to particular sections of the liner 30, such as the medial section along the longitudinal centerline of a diaper, to provide greater wettability of such sections.

The outer cover 48 may suitably be composed of a material which is either liquid permeable or liquid impermeable. It is generally desirable that the outer cover 48 be formed from a material which is substantially liquid-impermeable. For example, a typical outer cover 48 can be manufactured from a thin plastic film or other flexible liquid impermeable material. For example, the outer cover 48 may be formed from a polyethylene film having a thickness of from about 0.012 mm (0.5 mil) to about 0.051 mm (2.0 mils). If desirous of presenting the outer cover 48 with a more cloth-like feel, the outer cover 48 may include a polyethylene film having laminated to the lower or outer surface thereof a nonwoven web, such as a spunbond web of polyolefin fibers. For example, a polyethylene film having a thickness of about 0.015 mm (0.6 mil) may have thermally laminated thereto a spunbond web of polyolefin fibers, which fibers have a thickness of about 1.5 to about 2.5 denier per filament, which nonwoven web has a basis weight of about 24 gsm (0.7 osy). Methods of forming such cloth-like outer covers are known to those skilled in the art.

Further, the outer cover 48 may be formed of a woven or nonwoven fibrous web layer which has been totally or partially constructed or treated to impart a desired level of liquid impermeability to selected regions that are adjacent or proximate the absorbent structure 50. Still further, the outer cover 48 may optionally be composed of micro-porous "breathable" material, which permits vapors to escape from the absorbent structure 50 while still preventing liquid exudates from passing through the outer cover 48.

The absorbent structure 50 may include a matrix of hydrophilic fibers, such as a web of cellulosic fluff, mixed with particles of a high-absorbency material commonly known as superabsorbent material. In a particular version, the absorbent structure 50 includes a mixture of superabsorbent hydrogel-forming particles and wood pulp fluff. The wood pulp fluff may be exchanged with synthetic polymeric, meltblown fibers or with a combination of meltblown fibers and natural fibers. The superabsorbent particles may be substantially homogeneously mixed with the hydrophilic fibers or may be non-uniformly mixed. One suitable type of wood pulp fluff is identified with the trade designation CR-1654, available from Bowater, Inc., Greenville, S.C., and is a bleached, highly-absorbent sulfate wood pulp containing primarily soft wood fibers. A special densification pulp, identified with the trade designation ND-416, available from Weyerhaeuser of Federal Way, Washington, is also suitable for use.

To limit any undesired movement of superabsorbent material, the disposable diaper 20 may also include a wrap sheet (not shown) which is placed immediately adjacent and partially or totally around the entire absorbent structure 50, around an individual layer of the absorbent structure 50, or around one or more selected elements of the absorbent structure 50, as desired. The wrap sheet is typically a layer of absorbent material that covers at least the upper and lower surfaces of the absorbent structure 50 prior to the absorbent structure 50 being situated between the outer cover 48 and the liner 30.

The absorbent structure 50 may have any of a number of shapes. For example, the absorbent structure 50 may be rectangular, I-shaped or T-shaped. It is generally desired that the absorbent structure 50 be narrower in the crotch portion than the rear or front portion(s).

Figure 2:
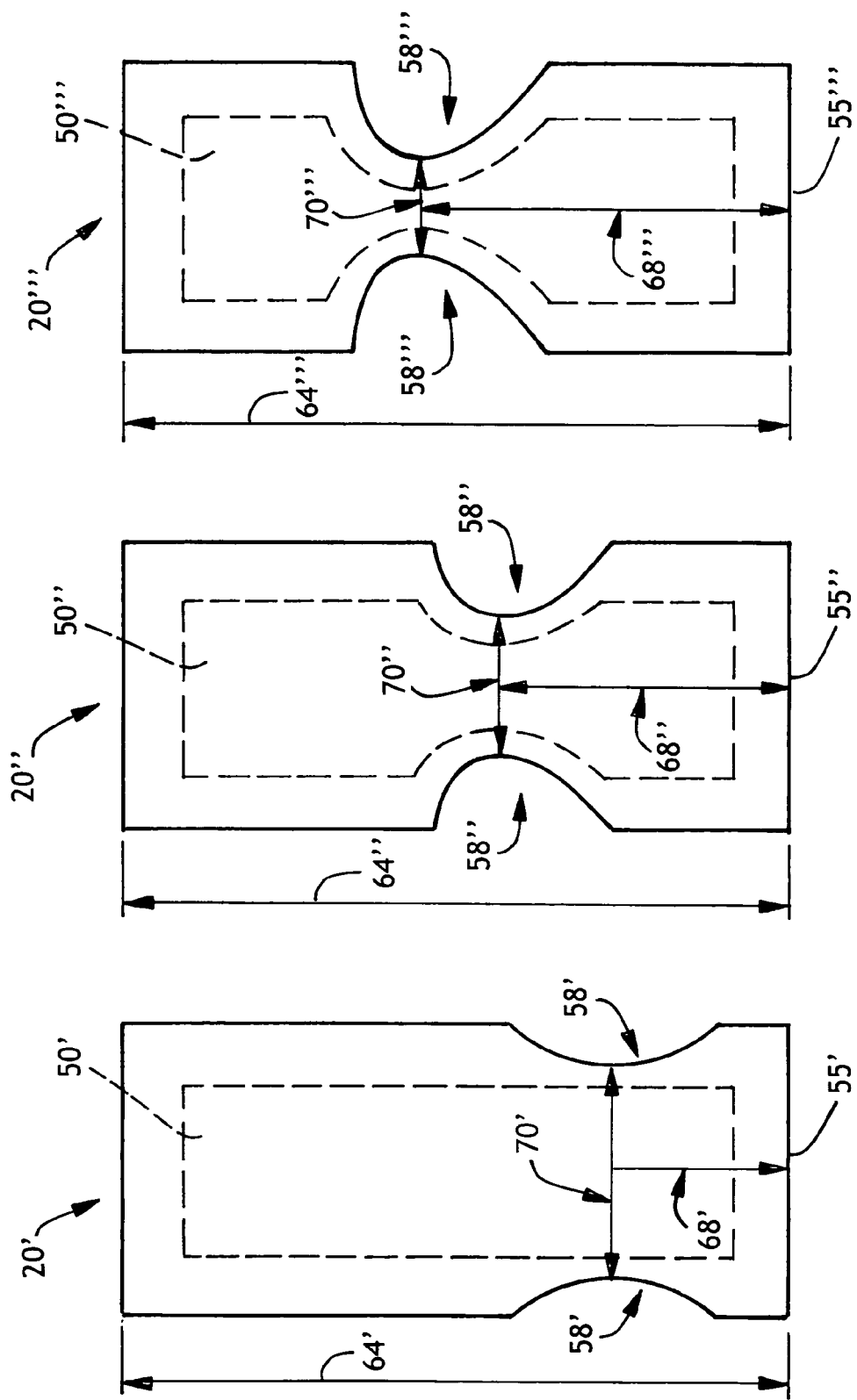
FIG. 2 illustrates an array of disposable absorbent articles of the present invention.

Referring to FIG. 2, an array of diapers is illustrated. The array includes three diapers 20, but an array of diapers in accordance with the present invention can include as few as two diapers and as many different diapers as necessary to address the needs of users with various predominant leg positions. Further the array illustrates a single first diaper 20', a single second diaper 20", and a single third diaper 20'". The array may include a plurality of first diapers 20', a plurality of second diapers 20", and a plurality of third diapers 20'", where all of the first diapers 20' have a similar configuration, all of the second diapers 20" have a similar configuration, and all of the third diapers 20'" have a similar configuration.

Each of the diapers 20 in the array may differ from the others in terms of leg opening longitudinal positioning ratio, leg opening lateral spacing, longitudinal length, and other features. The leg opening longitudinal positioning ratio (described in detail below) characterizes the relative distance of the leg openings from the front waist edge. The leg opening lateral spacing (described in detail below) is the width of the absorbent article measured at the leg openings. More particularly, a first diaper 20' may suitably have a leg opening longitudinal position relatively closer to the front waist edge 55 than a second diaper 20". The first diaper 20' therefore may be more appropriate for a newborn and the second diaper 20" may be more appropriate for an older infant. Thus, the leg opening longitudinal positioning may be correlated to the predominant leg positioning of the user providing an easier donning process, a more comfortable fit, and/or a better performing diaper. The predominant leg position of a user may change as the user develops from a newborn, to an infant, to a crawler, and finally to a toddler. Additionally, a user may have different predominant leg positions depending upon the specific activities of the user. For example, a crawling user may have a given predominant leg position while awake (legs perpendicular to the torso), and a different predominant leg position while sleeping (legs extended and parallel with the torso or legs tucked up close to the body).

Positioning of the leg opening 58 relatively close to the front waist edge 55 is suitable for newborn users because newborns typically maintain a fetal tuck when in a resting position (without external forces applied to the body). As the infant develops, the predominant leg position begins to relax and the legs and the knees gradually begin to move away from the chest in the resting position. For newborns, this aspect of the predominant leg positioning is not conducive to using large diapers that have been scaled down to a smaller size, as the leg openings may be too far from the front waist edge.

Due to the spread in birth weights, ranging from under 1 pound to over 10 pounds, as well as the varying rates at which newborns mature from one predominant leg position to another, the array of diapers having differing leg opening longitudinal positioning may be of a single size. The array is then suitable for a variety of children of a given size, each being in a different developmental stage, for example a one day old 10 pound baby, a two week old 10 pound baby, and a three month old 10 pound baby. Alternatively, the array of diapers having differing leg opening longitudinal positioning may be a number of sizes, such that the array is suitable for children of a given size being in a first developmental stage and children of a larger size being in a second developmental stage more advanced than the first. This second array may be suitable for a single child as they grow and develop.

FIG. 2 illustrates a first array of diapers including three diapers, 20', 20", and 20'". The first diaper 20' includes a first front end edge 55' and a first longitudinal length 64'. The first diaper 20' also includes a first pair of leg openings 58'. The first pair of leg openings 58' have a first leg opening median which is defined as the longitudinal position of the narrowest point of the diaper between the leg openings 58'. Where the diaper has a plurality of narrowest points, such as when the leg openings have linear portions parallel to the longitudinal length (see FIG. 3), the leg-opening median is defined as the longitudinal position of the midpoint of the linear portions parallel to the longitudinal length.

To characterize the positioning of the pair of leg openings 58, a longitudinal distance 68 from the leg-opening median to the front-end edge 55 is measured. To compare the leg opening positioning between diapers of different sizes, a leg opening longitudinal positioning ratio is calculated. The leg opening longitudinal positioning ratio is defined as the longitudinal distance 68 divided by the longitudinal length 64. The leg opening longitudinal positioning ratio can vary from near zero for leg openings 58 located very close to the front-end edge 55, to near 0.5 for leg openings 58 located in the longitudinal midpoint of the diaper 20, to finally near 1 for leg openings located longitudinally opposite the front-end edge 55.

Relatively small leg opening longitudinal positioning ratios (near zero) are beneficial for newborns and other users that have predominant leg positions with the legs and knees near the chest (in the fetal position). This allows for a large portion of the diaper to the rear of the pair of leg openings 58 to cover the buttocks of the user. It further allows a minimal amount of the diaper to the front of the pair of leg openings 58 to prevent squeezing between the legs and torso. Leg opening longitudinal positioning ratios near 0.5 are beneficial for toddlers or others that have predominant leg positions with the legs extended such that the legs are parallel to the upper torso. This allows for roughly an equal portion of the diaper to the rear of the pair of leg openings 58 to cover the buttocks and to the front of the pair of leg openings 58 to cover up to the user's waistline. Leg opening longitudinal positioning ratios in between zero and 0.5 are beneficial for users that have predominant leg positions such that the legs are perpendicular to the torso of the users, for example in users that are crawling. This allows for coverage of the buttocks to the rear of the pair of leg openings 58 and free movement for crawling.

FIG. 2 also illustrates a second diaper 20" having a second front end edge 55", a second longitudinal length 64", and a second pair of leg openings 58". The second pair of leg openings 58" have a second leg opening median located a second longitudinal distance 68" from the second front end edge 55". The second diaper 20" has a second leg opening longitudinal position ratio defined by the second longitudinal distance 68" divided by the second longitudinal length 64". The second leg opening longitudinal position ratio is larger than the first leg opening longitudinal ratio to fit users with predominant leg positions that are more extended than users of the first diaper 20'.

The first 20' and the second 20" diapers can be compared by dividing the second or larger leg opening longitudinal position ratio by the first or smaller leg opening longitudinal position ratio. The second leg opening longitudinal position ratio divided by the first leg opening longitudinal position ratio may be greater than 1.2, alternatively greater than 1.3, and finally greater than 1.4. A greater quotient indicates that the array will fit users with a wider range of predominant leg positions. This may provide caregivers the ability to select the best article for a given user during a particular developmental stage.

Diapers that are simply scaled down versions of one another will have first and second leg opening longitudinal position ratios that are very similar and therefore dividing the leg opening longitudinal position ratio of the second by that of the first will result in a value near 1. Such diapers may not be suited to provide benefits to users having different predominant leg positions.

FIG. 2 also illustrates a third diaper 20'" having a third front end edge 55'", a third longitudinal length 64'", and a third pair of leg openings 58'". The third pair of leg openings 58'" have a third leg opening median located a third longitudinal distance 68'" from the third front end edge 55'". The third diaper 20'" has a third leg opening longitudinal position ratio defined by the third longitudinal distance 68'" divided by the third longitudinal length 64'". The third leg opening longitudinal position ratio is larger than the second leg opening longitudinal ratio to fit users with predominant leg positions that are more extended than those of the user of either the first 20' or second 20" diaper.

The second 20" and the third 20'" diaper can be compared by dividing the third or larger leg opening longitudinal position ratio by the second or smaller leg opening longitudinal position ratio. The third leg opening longitudinal position ratio divided by the second leg opening longitudinal position ratio may be greater than 1.2, alternatively greater than 1.3, and finally greater than 1.4. By providing an array of three diapers 20', 20", 20'" with the design configurations as described, caregivers have the ability to select either an article designed for a user with the predominant leg position of a newborn, an article designed for a user with the predominant leg position of a crawler, or an article designed for a user with the predominant leg position of a walker. These options may provide an optimization in the articles relative to fit, leakage, comfort, and/or aesthetics for the user.

The size of the products, as measured by the longitudinal length 64, in the array may vary in many ways. For example, as illustrated in FIG. 2, the first longitudinal length 64', the second longitudinal length 64", and the third longitudinal length 64'" may be equal. This array of diapers 20 may be suitable for the same sized users that are in different stages of development. For example the first diaper 20' may be suitable for a 10 pound newborn, the second diaper 20" may be suitable for a 10 pound one month old, and the third diaper 20'" may be suitable for a 10 pound three month old.

Alternatively the first, second, and third longitudinal lengths 64', 64", 64'" may include two or more lengths. For example, the first longitudinal length 64' and the second longitudinal length 64" may be equal and the third longitudinal length 64'" may be greater than the first longitudinal length 64' and the second longitudinal length 64". This array may be suitable for a given user that matures quickly from the first size/longitudinal length 64' to the second size/longitudinal length 64" without growing substantially. That is, the user's predominant leg position changes, without significant growth of the user. The user then grows, in addition to maturing into the third size/longitudinal length 64'". That is, the user's predominant leg position changes in conjunction with an increase in user size. Situations may exist were the first longitudinal length 64' is greater than the second longitudinal length 64", for example where additional coverage is need in the first diaper 20'. In diapers that are designed to fit users as they grow, the second longitudinal length 64" divided by the first longitudinal length 64' may be less than 2.0, alternatively less than 1.5, and alternatively less than 1.25. Likewise, the third longitudinal length 64'" divided by the second longitudinal length 64" may be less than 2.0, alternatively less than 1.5, and alternatively less than 1.25. These size differences allow for a user to advance directly from the first diaper 20' to the second diaper 20" as they grow.

As a user develops and the legs progress from a fetal position to a fully extended position with the legs extended from and parallel to the torso, the lateral space between the legs may decrease. One way of accommodating for this change, while maintaining the aesthetics and fit of the diaper, is to reduce the amount of the diaper between the legs, as measured by the leg opening lateral spacing 70. The leg opening lateral spacing 70 is defined by the narrowest width of the diaper located between the pair of leg openings 58. For example, the first pair of leg openings 58' of the first diaper 20' may have a first leg opening lateral spacing 70', and the second pair of leg openings 58" of the second diaper 20" may have a second leg opening lateral spacing 70". To accommodate for a smaller lateral space between the legs in a more developed user, the first or larger leg opening lateral spacing 70' divided by the second or smaller leg opening lateral spacing may be greater than 1.1, alternatively greater than 1.2, and finally greater then 1.3. Further, the third pair of leg openings 58'" of the third diaper 20'" may have a smaller third leg opening lateral spacing 70'". The second leg opening lateral spacing 70" divided by the third leg opening spacing 70'" may be greater than 1.1, alternatively greater than 1.2, and finally greater then 1.3. These options provide for more diaper between the legs of the user where the legs are closer to the fetal position (which may correspond to a less mobile user), and less diaper between the legs of the user where the legs are closer to a fully extended position (which may correspond to a more mobile user).

Figure 3:
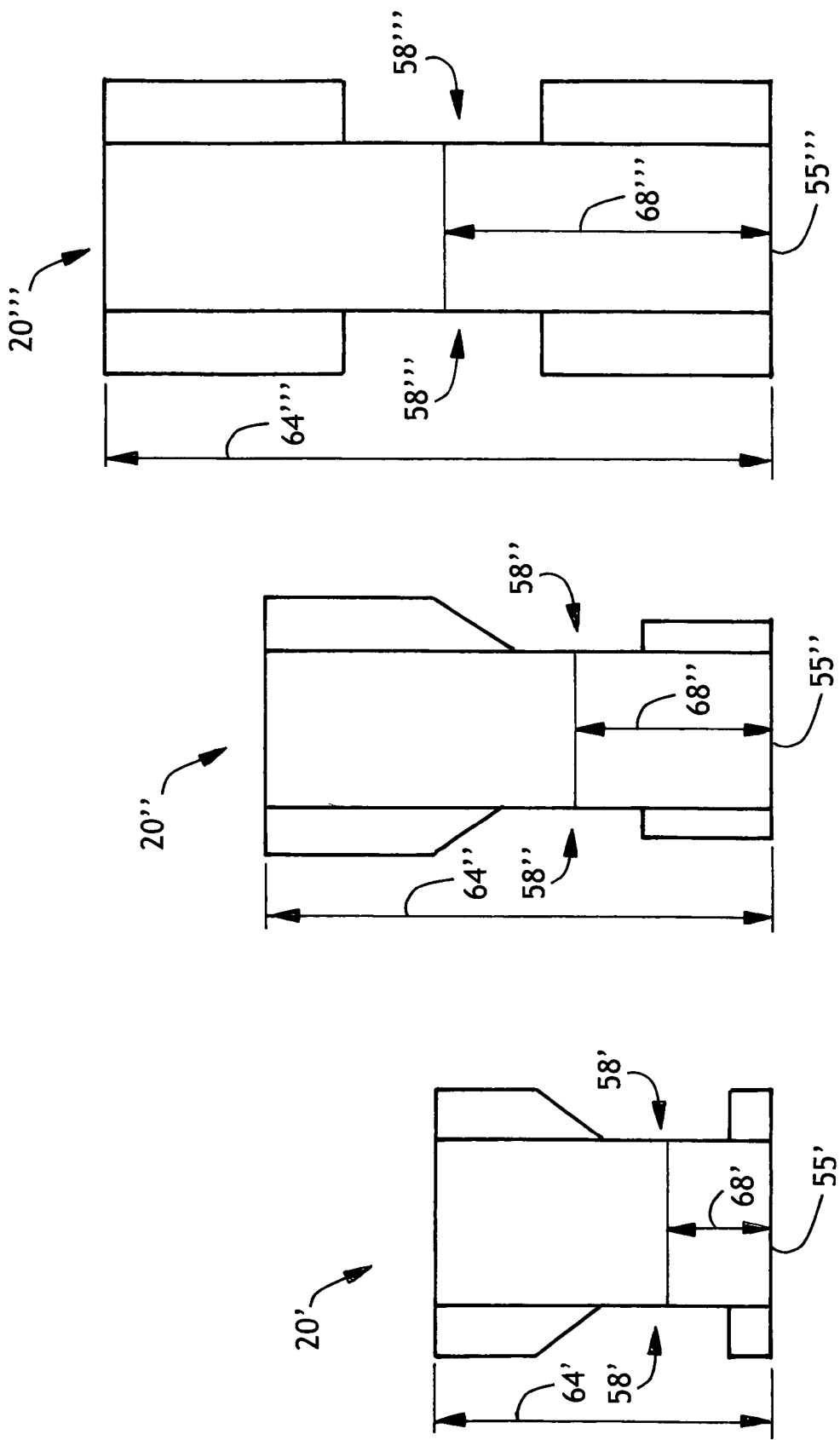
FIG. 3 illustrates a second array of disposable absorbent articles of the present invention.

The leg opening 58 may have multiple shapes. The leg opening 58 may have portions that are arcuate (FIG. 2). The leg opening 58 may have portions that are linear (FIG. 3). The leg opening 58 may have portions that are arcuate and portions that are linear depending on the specific design of the diaper 20 and the intended user. The leg opening 58 may be formed by removing material from the side edges of the diaper (FIG. 2). Alternatively, the leg opening may be formed by attaching pieces of material to the side edges of the diaper in front of and behind the resulting leg opening 58 (FIG. 3). The specific design, shape, and size of the leg opening 58 may be adjusted depending on the method utilized to manufacture the diaper, and the intended end user.

As further illustrated in FIG. 2, the array of diapers 20', 20", 20'" may have additional features that change from one diaper to the next. For example, as illustrated, the first absorbent structure 50' in the first diaper 20' may have a rectangular shape, with linear side edges. The second absorbent structure 50" in the second diaper 20" may have a slight hourglass shape, with small indentations for the legs of a user such that the narrowest width of the second absorbent structure 50" is less than 80% of the widest width of the second absorbent structure 50". Further, the third absorbent structure 50'" in the third diaper 20'" may have large indentations for the legs of a user such that the narrowest width of the third absorbent structure 50'" is less than 70% of the widest width of the third absorbent structure 50'".

FIG. 3 illustrates a second array of diapers including three diapers, 20', 20", and 20'". As illustrated in FIG. 3, the leg openings have linear portions parallel to the longitudinal length. As stated above, and illustrated in FIG. 3, the leg-opening median is defined as the longitudinal position of the midpoint of the linear portions parallel to the longitudinal length.

The second array of diapers 20', 20", 20'" illustrated in FIG. 3 is similar to the array of diapers illustrated in FIG. 2 with regard to the leg opening longitudinal positioning. The diapers illustrated in FIG. 3 differ from the diapers illustrated in FIG. 2 in that the leg openings are defined in part by front and rear ears that are attached to the side edges of the chassis of the diapers 20', 20", 20'". The front and rear ears may be of any shape. The front and rear ears may be rectangular, alternatively, they may be rectangular with portions of either the front or rear rectangle removed to produce a shaped ear. The array illustrated in FIG. 3 also differs from the array in FIG. 2 in that the diapers 20', 20", 20'" differ in longitudinal length 64. The first diaper 20' being shorter than the second diaper 20" and the second diaper 20" being shorter than the third diaper 20'". As described above, the length of diapers of the array may vary in any way as suitable depending on the specific intended use.

In carrying out the method of the invention, information regarding correlations between a user's predominant leg position and the appropriate diaper from the array may be made available to consumers contemplating the purchase of one of the diapers in the array.

The key information to be communicated to the caregiver is designed to help the caregiver be aware of when the child is ready to switch to a different configuration of diaper. For example the information may describe the predominant leg position of a user that indicates greater applicability of one of the diapers in the array over another diaper in the array. Modes of conveying information to the caregiver that may help the caregiver determine the appropriate diaper may include in-store displays, posters, computer programs, brochures, package literature, shelf information, videos, and information on the back of coupons, or any other suitable form of communication. The information could be available at stores, on television, in computer-friendly form, in advertisements, or through any other appropriate venue.

As various changes could be made in the above constructions without departing from the scope of the invention, it is intended that all matter contained in the above description or shown in the accompanying drawings shall be interpreted as illustrative and not in a limiting sense.

What is claimed is:
1. An array of disposable articles, the array contemporaneously manufactured by or for the same business entity, comprising:
 a first disposable article comprising:
  a first front end edge;
  a first longitudinal length;

a first pair of leg openings having a first leg opening median located a first longitudinal distance from the first front end edge; and
a first leg opening longitudinal position ratio defined by the first longitudinal distance divided by the first longitudinal length; and
a second disposable article comprising:
a second front end edge;
a second longitudinal length;
a second pair of leg openings having a second leg opening median located a second longitudinal distance from the second front end edge; and
a second leg opening longitudinal position ratio defined by the second longitudinal distance divided by the second longitudinal length;
wherein the second leg opening longitudinal position ratio divided by the first leg opening longitudinal position ratio is greater than 1.2.

2. The array of claim 1 further comprising a third disposable article comprising:
a third front end edge;
a third longitudinal length;
a third pair of leg openings having a third leg opening median located a third longitudinal distance from the third front end edge; and
a third leg opening longitudinal position ratio defined by the third longitudinal distance divided by the third longitudinal length;
wherein the third leg opening longitudinal position ratio divided by the second leg opening longitudinal position ratio is greater than 1.2.

3. The array of claim 1 wherein the second longitudinal length is greater than the first longitudinal length.

4. The array of claim 1 wherein the first longitudinal length is greater than the second longitudinal length.

5. The array of claim 1 wherein the first longitudinal length is equal to the second longitudinal length.

6. The array of claim 2 wherein the first longitudinal length is the same as the second longitudinal length and the third longitudinal length is greater than the first longitudinal length and greater than the second longitudinal length.

7. The array of claim 1 wherein the first pair of leg openings have a first leg opening lateral spacing, the second pair of leg openings have a second leg opening lateral spacing, the first leg opening lateral spacing divided by the second leg opening lateral spacing is greater than 1.1.

8. The array of claim 1 wherein the first pair of leg openings has portions that are arcuate.

9. The array of claim 1 wherein the first pair of leg openings has portions that are linear.

10. The array of claim 9 wherein the portions that are linear are parallel to the first longitudinal length and the portions that are parallel to the first longitudinal length have a midpoint which defines the first leg opening median.

11. The array of claim 1 wherein the first disposable article is a diaper.

12. The array of claim 1 wherein the second disposable article is a training pant.

13. The array of claim 1 comprising a plurality of first disposable articles having a first similar configuration and a plurality of second disposable articles having a second similar configuration.

14. A method of providing an array of disposable absorbent articles, the array contemporaneously manufactured by or for the same business entity, comprising:
providing an array of at least two different disposable articles, the array comprising:
a first disposable article comprising:
a first front end edge;
a first longitudinal length;
a first pair of leg openings having a first leg-opening median located a first longitudinal distance from the first front end edge; and
a first leg opening longitudinal position ratio defined by the first longitudinal distance divided by the first longitudinal length; and
a second disposable article comprising:
a second front end edge;
a second longitudinal length;
a second pair of leg openings having a second leg opening median located a second longitudinal distance from the second front end edge; and
a second leg opening longitudinal position ratio defined by the second longitudinal distance divided by the second longitudinal length;
wherein the second leg opening longitudinal position ratio divided by the first leg opening longitudinal position ratio is greater than 1.2; and
conveying information to a consumer describing the predominant leg position of a user that indicates greater applicability of one of the disposable articles in the array over another disposable article in the array.

15. The method of claim 14, wherein the information is conveyed by at least one of the group consisting of in-store displays, posters, brochures, package literature, shelf information, computer programs, videos, television advertisements, coupons, and other advertisements.

16. The method of claim 14 wherein the array further comprises a third absorbent article comprising:
a third front end edge;
a third longitudinal length;
a third pair of leg openings having a third leg opening median located a third longitudinal distance from the third front end edge; and
a third leg opening longitudinal position ratio defined by the third longitudinal distance divided by the third longitudinal length;
wherein the third leg opening longitudinal position ratio divided by the second leg opening longitudinal position ratio is greater than 1.2.

17. The method of claim 14 wherein the first pair of leg openings have a first leg opening lateral spacing, the second pair of leg openings have a second leg opening lateral spacing, the first leg opening lateral spacing divided by the second leg opening lateral spacing is greater than 1.1.

18. The method of claim 14 wherein the first pair of leg openings have portions that are arcuate.

19. The method of claim 14 wherein the first pair of leg openings have portions that are linear.

20. The method of claim 19 wherein the portions that are linear are parallel to the first longitudinal length and the portions that are parallel to the first longitudinal length have a midpoint which defines the first leg opening median.

21. An array of disposable articles, the array contemporaneously manufactured by or for the same business entity, comprising:
a plurality of first disposable articles having a first similar configuration, the first disposable articles comprising:
a first front end edge;
a first longitudinal length;
a first pair of leg openings having a first leg opening median located a first longitudinal distance from the first front end edge; and a first leg opening longitudinal position ratio defined by the first longitudinal distance divided by the first longitudinal length; and a plurality of second disposable articles having a second similar configuration, the second disposable articles comprising:
  a second front end edge;
  a second longitudinal length;
  a second pair of leg openings having a second leg opening median located a second longitudinal distance from the second front end edge; and
  a second leg opening longitudinal position ratio defined by the second longitudinal distance divided by the second longitudinal length;
wherein the second leg opening longitudinal position ratio divided by the first leg opening longitudinal position ratio is greater than 1.2, the first pair of leg openings has portions that are arcuate, and the second pair of leg openings has portions that are arcuate.

* * * * *